United States Patent [19] [11] 4,158,536
Willay et al. [45] Jun. 19, 1979

[54] APPARATUS FOR THE AUTOMATIC PREPARATION AND MOLDING OF SAMPLES FOR X-RAY ANALYSIS

[76] Inventors: Gerard Willay, Rte. d'Ars, Ars sur Moselle, France; André Wittmann, 4, place du Général de Gaulle, Metz, both of France

[21] Appl. No.: 859,150

[22] Filed: Dec. 9, 1977

[30] Foreign Application Priority Data

Dec. 15, 1976 [FR] France .................................. 76 37853

[51] Int. Cl.² .......................... B29F 5/00; B29C 11/00
[52] U.S. Cl. ..................................... 425/169; 425/200
[58] Field of Search ................................. 425/169, 200

[56] References Cited

U.S. PATENT DOCUMENTS

| | | | |
|---|---|---|---|
| 3,526,926 | 9/1970 | Reid | 425/200 X |
| 3,567,929 | 3/1971 | Barker et al. | 425/169 X |
| 3,904,723 | 9/1975 | Prince | 425/200 X |
| 4,017,228 | 4/1977 | Areijo et al. | 425/169 X |
| 4,086,044 | 4/1978 | Sikora | 425/169 X |

Primary Examiner—J. Howard Flint, Jr.
Attorney, Agent, or Firm—Kurt Kelman

[57] ABSTRACT

Apparatus for the automatic preparation of samples for analysis comprises a tubular fusion furnace and a casting device. The furnace is horizontally disposed and permits introduction and removal of crucibles with samples through its two open ends. Transport equipment assures a periodical progression of the crucibles in the interior of the tubular furnace in successive and repeating states. The samples are agitated during momentary stops of the crucibles in their periodic progression.

8 Claims, 3 Drawing Figures

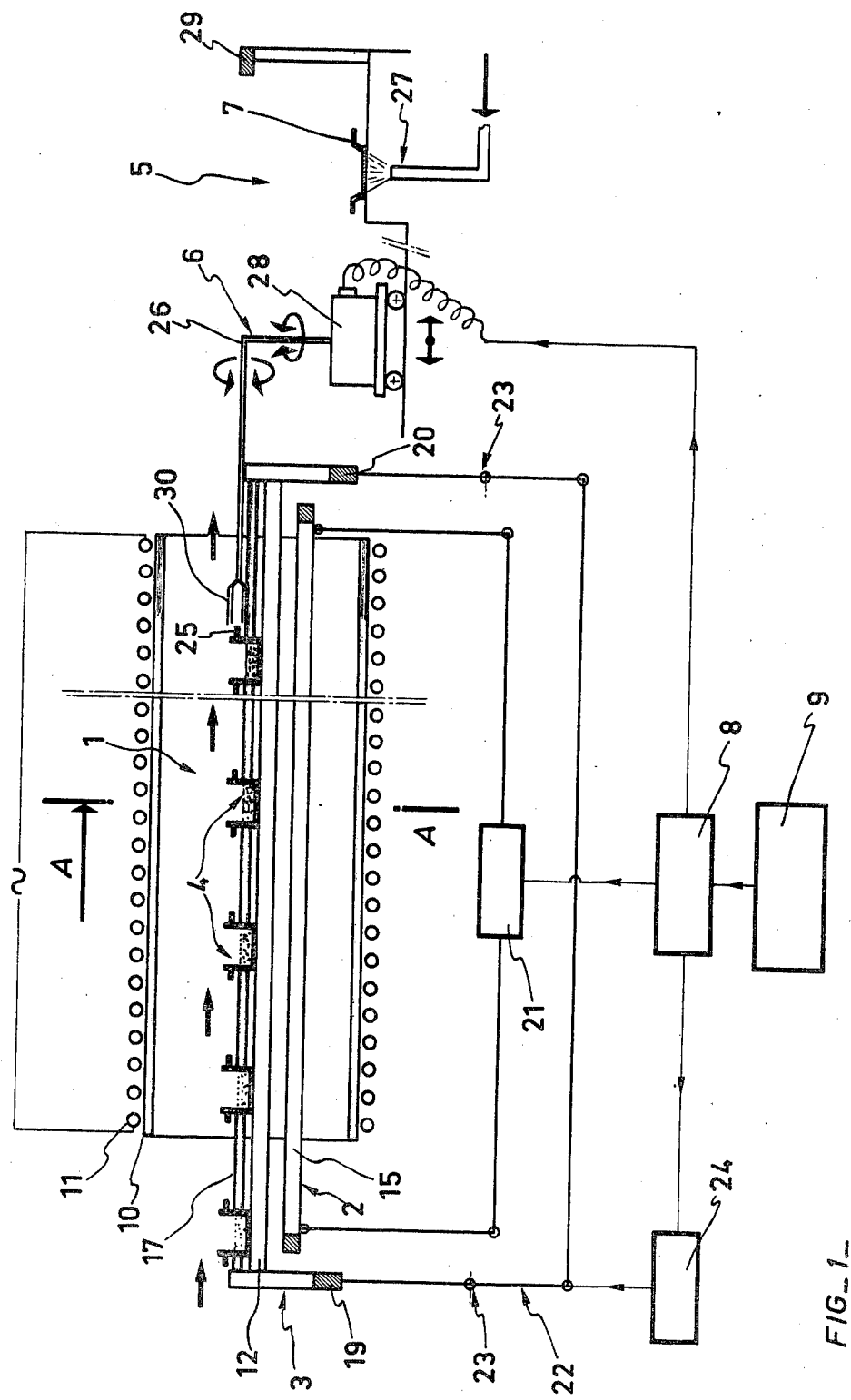
FIG._1_

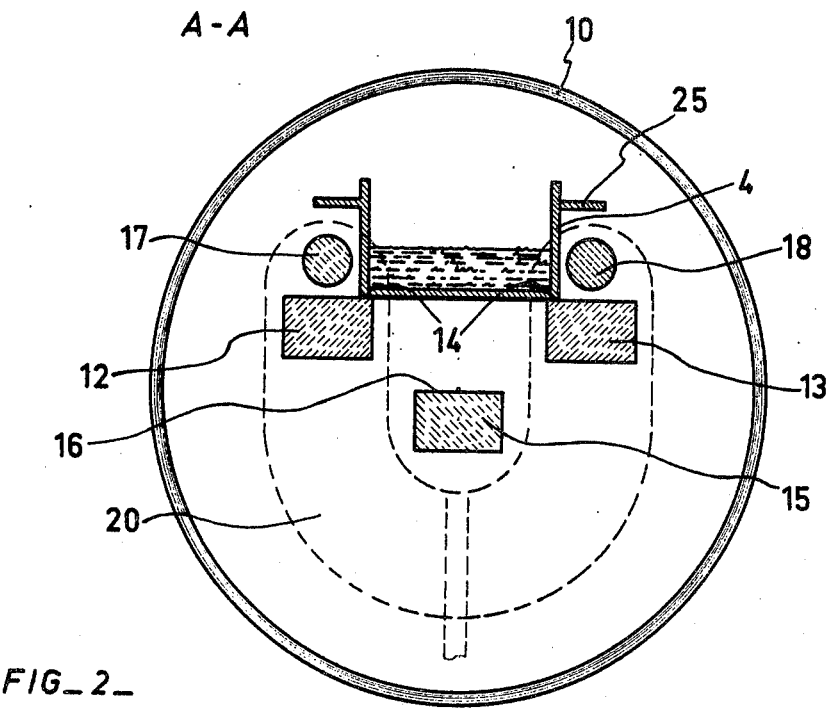
FIG_2_
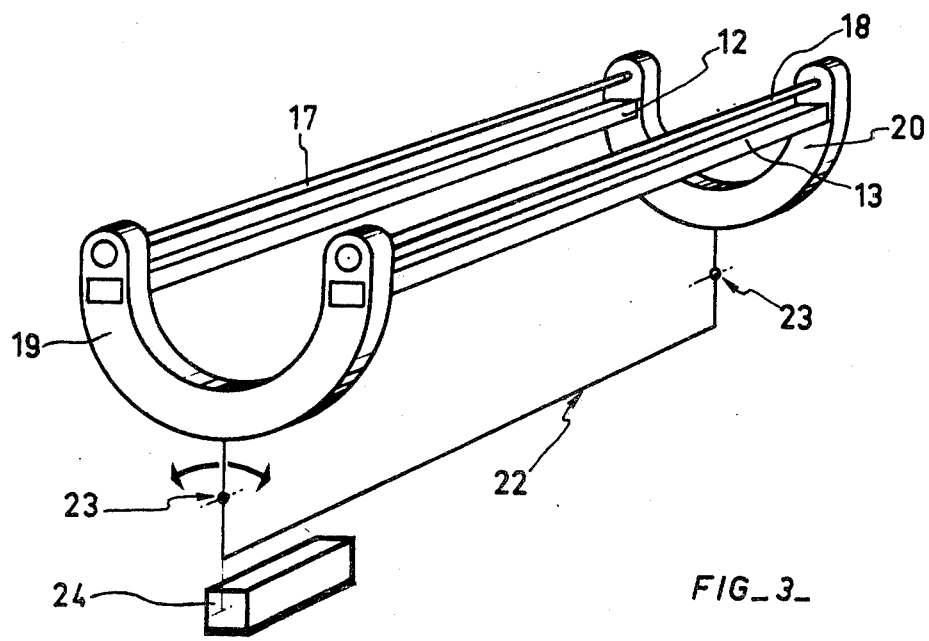
FIG_3_

APPARATUS FOR THE AUTOMATIC PREPARATION AND MOLDING OF SAMPLES FOR X-RAY ANALYSIS

The present invention relates to an apparatus for the automatic preparation of samples and, in particular, for the preparation of samples of non-metallic products destined for analysis by the fluorescence of X-rays.

It is known that the accurate analysis of the composition of products and particularly of non-metallic products by fluorescence of X-rays cannot be realized without careful preparation of the sample, with transformation into a very homogenous and easily manipulatable vitreous material. These requirements constitute a handicap for the large-scale use of X-ray fluorescence for production control in view of the slowness of the manual operating procedures and the rigor which is required in their execution.

An apparatus for the automatic preparation conceived and developed with a view to replace the manual operating procedure is known. This apparatus, described in the review "X-Ray spectrometry, 1974"—Vol. 3, pages 137 to 142, is comprised of three essential parts each assuring a predetermined function:

a fusion furnace essentailly constituted by an induction coil fed by a high-frequency current and heating a crucible disposed in the interior, containing the material to be prepared for the analysis. The crucible is supported by a vertical jack which may effect alternating rotational movements about its axis to assure the homogenization of the sample.

a casting device constituted by the combination of a high-frequency induction furnace in which a casting vessel is placed with a view of being preheated, and a clamping element capable of seizing the crucible after fusion and to pour its content into the said vessel by pivoting of the crucible.

a pneumatic unit comprising a series of jacks which assure all the necessary movements for the operation of the apparatus and the sequence of manufacture. A logical programmer assures its automatic control.

The functional parts mentioned hereinabove and particularly the two first ones which determine the productivity of the apparatus operate discontinuously or "blow by blow", that is they treat a single sample at any one time. This leads to an operation of the apparatus producing of the order of one sample every eight minutes, at best, which has proven generally insufficient, considering present-day production requirements.

The present invention has as its object to improve the rapidity of the production of analytical samples substantially without harming the quality requirements for their preparation.

For this purpose, the invention provides an apparatus for the automatic preparation of samples, particularly for analysis by fluorescence of X-rays, comprising a fusion furnace, a casting device and means for the automatic control of the unfolding of the manufacturing sequences, characterized in that the fusion furnace is constituted by a heating enclosure of tubular form, horizontally disposed and open at its two ends to permit, respectively, the introduction and the removal of crucibles in alignment and in that means are provided for transporting the crucibles into the interior of the heating enclosure in progressive manner in successive stages, and means for agitating the samples at momentary stops in their progression.

According to a preferred characteristic of the invention, the transport means are constituted by two distinct parts, respectively mobile and fixed, in the longitudinal direction of the enclosure, and respectively assuring the transfer of the crucibles in series during their progression in successive stages and their support during the momentary stops in their progression.

According to a preferred embodiment, the mobile part, assuring the progressive transfer of the crucibles, is constituted by one or several small horizontal beams one in prolongation to the other and being axially movable in the direction of the ends of the enclosure; the fixed part, which assures the support of the crucibles during their stop, is constituted by two beams extending at least over the entire length of the enclosure, separated from each other a distance smaller than the width of the crucibles, oriented parallel to the small transfer beam mentioned hereinabove and respectively disposed at either side of the latter, same also presenting the possibility of moving vertically so that it may be raised or lowered with respect to the support beams. Like the small transfer beams, they have at the upper portion a flat support surface on which the crucibles rest.

According to a modified embodiment, the mobile part assuring the progressive transfer of the crucibles is constituted only by a single small beam which extends at least over the entire length of the enclosure.

According to a supplementary characteristic, the heating enclosure also comprises means for guiding the crucibles.

According to a particular disposition, these guidance means are constituted by two horizontal slideways extending at least over the entire length of the enclosure and respectively disposed on either side of the crucibles in alignment, at a small distance from the latter, and above each of the two afore-mentioned support beams.

According to another preferred modification of the invention, the means for agitating the samples are mechanical means transversely movable in relation to the heating enclosure and providing a pivoting of the crucibles alternating from one side to the other in the direction of displacement by means of an intermediate transverse oscillating movement of the assembly constituted by the support beams and the guiding slideways, at the momentary stoppage of the progression of the crucibles in successive stages.

According to a particularly embodiment, the support beams and the guiding slideways, extending substantially outside the enclosure at one side and the other, are assembled at their ends by mobile arches rotatable about a longitudinal axis of the enclosure.

As will be understood, the present invention envisages thus an apparatus for the "chain" preparation of samples. The speed of the production is further increased by means of a tunnel-type fusion furnace in continuous operation for permanently treating a plurality of crucibles in alignment.

One of the essential characteristics of the invention resides in the manner of transporting the crucibles through the fusion furnace constituted by a horizontal tubular heating enclosure. In substance, this transport operates in a succession of longitudinal displacements in the real sense of the phrase, alternating with phases of stoppage during which take place the homogenizing operations by the agitation of the material contained in the crucibles and whose fusion is produced progressively between the introduction and the middle of the surrounding furnace.

Starting from such a general definition of the invention, numerous and varied embodiments may be conceived which are known means for realizing progressive operations. For example, the transport of the crucibles may be effected by a conveyor belt on metallic rollers or any other similar means.

However, this manner of dispositions presents a certain number of inconveniences of which the most important are the risks of elongation of the belt by thermal expansion, the lack of stability of the crucibles or technological difficulties to obtain agitation of the crucibles without having to move the entire furnace assembly.

Therefore, one may also envisage agitating means other than mechanical, such as electromagnetic, for example. The advantage would be to act directly on the content of the crucible while the latter remains immobile.

However, it would be necessary, for thermal reasons, to cool the electrical conductors, which implies the creation of zones of considerable temperature gradients producing a lowering of the calorifiic output of the furnace and a supplemental energy expense if it is desired to maintain desired temperatures at the level of the curcibles. Furthermore, means for stirring by induction are not of general application: it is, in fact, indispensible to obtain the desired effect that the treated material has good current conductivity. This is not the case generally, particularly for samples of non-metallic products destined for analysis by the fluorescence of X-rays with which the present application deals.

Without condemning the use of such means, the applicant nevertheless knows of the utilization of a transport called "step by step", furnaces "with beams" or "with mobile stringers" which are presently industrially used, particularly in metallurgy for preheating ingots or slabs of steel before they are rolled.

The adaptation, for the purpose of this invention, of this type of furnace consists in disposing fixed "support" beams serving for the placing of the crucibles and which extend in the longitudinal direction of the heating enclosure, and a "transport" beam parallel to the first ones, disposed therebetween and capable of being raised and lowered vertically as well as advanced and retracted longitudinally. The displacement of the crucibles is then effected (according to the accepted expression "step by step") by a cyclic movement of the transport beam in a circular reciprocation or in a square cycle or in a combination of the two. These types of movements are well known in the state of the art and their more detailed description will be taken up in the course of the following description. The crucibles thus progress across the enclosure in a regular but discontinuous manner according to the alternation of transfer periods proper and periods of rest. The latter according to the invention are used to effectuate the homogenization of the charge of the crucibles which is progressively heated to fusion during the passage through the enclosure.

This homogenization is obtained by mechanical agitation of the crucibles when they rest on the support beams.

The desired agitation is obtained by an oscillation of the support beams about a longitudinal axis. An alternating pivoting of the crucibles from one side to the other in the direction of their displacement results therefrom and, accordingly, a mixing of the charge they contain.

As may be understood, such shaking may damage the stability of the crucibles. This risk is avoided by disposing on both sides of the crucibles and immediately adjacent thereto support bears serving as guards during the pivoting operating and playing the role of slideways during the periods of the longitudinal displacement.

It should be noted that the "transport" beam mentioned hereinabove which, for obvious reasons, must extend (as do the support beams) at least over the entire length of the enclosure may be replaced by several shorter beams longitudinally aligned. The cost of such a disposition is justified primarily for the transport of heavy charges, which is not the case in the invention. Another advantage, which may be of interest in the invention, resides in the fact that the stoppage time of the crucibles may be shortened by means of a suitable organization of the movement of the assembly. These variations in the realization are within the skill of the art and one may obtain here from a more detailed description.

It should also be noted that the heating enclosure may also have numerous modifications to the extent that it defines a tubular space brought to a high temperature, that is above the fusion temperature of the samples, and across which crucibles may be moved in line.

Thus, a simple resistance heater with a solenoid may be used. However, to limit thermal losses and to avoid the oxidation of the material consituting the solenoid, particularly by vapors emanating from the fusion of the samples, the applicant prefers to confine the said space by a tubular envelope, preferably of refractory material, and surrounded by an electric resistance.

The invention will now be well understood and its different aspects and advantages will more clearly emerge from the following description given by way of example of a particular embodiment, in no way limitative, and with reference to the accompanying sheets of drawings wherein:

FIG. 1 represents a longitudinal section of an apparatus according to the invention, FIG. 2 represents a transverse section along the plane A—A of FIG. 1, FIG. 3 represents a perspective view of the agitating means for the crucibles.

Referring to FIG. 1, it is seen that the apparatus is comprised of a furnace 1 equipped with transport and agitating means 3 for the aligned crucibles 4, and a casting device 5 represented schematically by a forked element 6 capable of seizing the crucibles before they leave the furnace and to pour their content into a vessel 7 previously heated and cooled with compressed air after the casting. The assembly is connected to an element 8 for the automatic control of the operations, which is itself connected to a logic programmer 9 assuring the automatic control of the assembly.

Reference will now be had to all three figures simultaneously. The furnace 1 is constituted by a cylindrical envelope 10 of aluminum or silicon carbide or another suitable refractory material. This envelope (or enclosure) is horizontally disposed and has a length of about 65 cm. The heating means are constituted by an electrical resistance 11 (FIG. 1) surrounding the envelope. Electricity is fed at a voltage of 220 V at an industrial frequency (50 Hz).

The interior of the enclosure comprises means for supporting the crucibles 4 in alignment, for transporting them and for agitating them:

the support means are constituted by two parallel carrying beams 12 and 13 fixed in the longitudinal direction of the heating enclosure 10 and extending the entire length of the latter beyond both of its ends to the exterior and, as particularly shown in FIG. 1, to the inlet end for permitting the charging of the crucibles. As can be seen in FIG. 2, these two beams (of refractory material) are separated from each other a distance less than the width of the crucibles and have flat upper faces which serve as support surfaces for the crucibles through their bottom 14.

the transport means are constituted by a small mobile beam 15, also of refractory material, and movable longitudinally as well as vertically between the support beams 12 and 13 by motor 21 (FIG. 1). As will be understood, this small transport beam 15 carries the crucibles as soon as it is raised above the fixed beams 12 and 13. For this purpose, it has a flat upper surface on which the crucibles may be rested when they are displaced. As can be seen from FIG. 1, the small beams 15 is extended at both ends to the exterior of the heating enclosure 10 and, particularly, as is shown in FIG. 1, to the inlet end to permit charging of the crucibles.

To increase the stability of the crucibles on the small beam 15 at the time of their displacement, parallel longitudinal bars 17 and 18 have been provided which serve as slideways. These bars are respectively disposed above each of the beams 12 and 13 at both sides of the crucibles and immediately adjacent thereto.

The mechanical agitating means for the crucibles are constituted by a cradle composed of two arches 19 and 20 respectively disposed facing each end of the heating enclosure 10 and interconnected by support bars 12 and 13 and by the corresponding slideways 17 and 18.

This cradle is integral with a mobile connecting rod system 22 effectuating a transverse oscillating movement about a fixed point 23 under the action of a motor 24. As will be understood, this results in a pivoting movement of the crucibles 4 alternating from one side to the other in their direction of displacement.

The operation of the apparatus for the manufacture of samples (or pearls) destined for analysis by fluorescence of X-rays will not be described.

The non-metallic product to be analyzed is finely comminuted, then roughly mixed with a flux in respective amounts of about 200 mg per 3 to 4 grams of flux. The initial mixture is poured into a crucible 4 which is subsequently introduced into the heating enclosure 10 maintained at a constant temperature of about 1100°–1150° C. and where the progressive fusion of the mixture is effected and, at the start, the dissolving of the powder in the flux. The crucibles are manually disposed on the exterior extensions of beams 12 and 13 downstream of the furnace. Their progression "step by step" across the heating enclosure 10 is assured by the small transport beam 15 which effects a movement in a "stepped cycle". This cyclic movement may be broken down into the following successive and repeating phases:

a phase of taking up the crucibles by a vertical upward movement of the small beam 15 so that is upper part 16 is raised above the beams 12 and 13. It is understood that this movement, nevertheless, has a sufficiently reduced amplitude so that the bars 17 and 18 may continue to play their role as slidways.

a phase of longitudinally transporting the crucibles in the direction of the outlet end of the enclosure by a horizontal reciprocating movement of the small beam 15 for a distance of about 6 cm.

a phase of depositing the crucibles on the support beams by a vertical descending movement of the small beam 15.

a phase of returning the small beam 15 to its initial position by a horizontal reciprocating movement below the beams 12 and 13 and in the direction of the inlet end of the heating enclosure.

It will thus be understood that the crucibles which are disposed one after the other in alignment traverse the heating enclosure in a progression in successive stages, alternating with periods of stoppage during which the lower return of the small transport beam is efffectuated.

During these periods of stoppage, the crucibles resting on the support beams 12 and 13 are subjected to a pivoting movement from one side to the other in their direction of advancement. This movement is made possible by an oscillation of the arches 19 and 20 integral with the assembly constituted by the transport beams 12, 13 and the slideways 17 and 18, which thus assume the function of a guard-rail or a balustrade preventing gliding and dropping of the crucibles.

The amplitude of the pivoting movement of the latter corresponds to an angle of rotation of the order of 15° with respect to the vertical. Since the crucibles are filled to about one sixth of their maximum capacity, there is no risk of spilling to be feared. The alternating cycle of the cradle constituted by the beams 12, 13 and the slideways 17, 18 is of the order of 12 per minute.

Summarizing, the crucibles aligned in the fusion furnace 1 are thus subjected, on the one hand, to a thermal action by progressive heating in the furnace and in accordance with their advancement in the enclosure 10 to attain, about in the middle of the furnace, a temperature of the order of 1100°–1150° C., a temperature at which the materials to be analyzed are in the liquid state, and, on the other hand, to a mechanical action which is operationally broken down into two successive and repeating periods:

a period of partial transport of the assembly of crucibles present at any moment on the fixed support beams 12 and 13, which partial transport is effected over about one tenth of the length of the enclosure by the longitudinal displacement of the small beam 15 in the high position.

a period of homogenization of the material contained in the crucibles by a mechanical agitation of the latter according to a movement of transverse oscillations of the support beams 12 and 13 on which they rest between two periods of partial transport. This period of agitation takes place during the lower return stroke of the reciprocation of the small beam 15, which is sufficently small not to interfere with the alternating rotational movements. At about 10 cm from the outlet of the furnace 1, the crucibles equipped with a small collar 25 are disposed by the small beam 15 in a longitudinal forward movement in the high position on the branches of a mobile element 6 with a double fork comprising an arm 26 for penetrating into the enclosure. This element then effectuates a recoil movement so as to position itself above a vessel 7 preheated by any appropriate means, then effectuates a rotary movement about its arm 26 so as to pour the contents of the crucibles into the vessel 7 where the solidification of the sample (or pearl) takes place by the cooling of the vessel under the action of a blast of compressed air, schematically shown at 27. The casting element 6 is put in motion by the motor 28. Once solidfied, the pearl is recovered by a suction device (not shown) without touching the vessel which is generally of a platinum or rhodium alloy. At the end of the casting, the mobile element 6 resumes its recoil movement, passes to a fixed abutment schematically shown at 29 which makes the empty crucible fall into a recovery receptacle (not shown) from where, after cooling, it may be cleaned and filled again with products to analyze and recycled to the inlet of the furnace.

The motors 21, 24 and 28 respectively assure the transport, oscillation and casting movements and are connected to a control element 8 which is itself connected to a programmer 9 which assure the automatic control of the assembly of the apparatus according to the mode of operation previously described.

The apparatus according to the invention has general application for the automatic production of samples destined for analysis when it is necessary to prepare them by dilution, followed by fusion.

Consequently, it is applicable particularly to the manufacture of pearls for the analysis by fluorescence of X-rays, being particularly convenient for most non-metallic products of siderurgy such as minerals, agglomerates, slags, refractories, etc.

The productivity in making pearls is substantially increased as compared to that with previously known devices. One passes thus from one pearl every 8 minutes to one pearl about every 3 minutes, and the dwell time of a crucible in the furnace is of the order of 20 to 25 minutes. The cycle of 3 minutes is conditioned by the casting time (about 10 sec.), the time for cooling in the vessel (about 2 min.), the removal of the pearl (about 5 sec.) and the delay in preheating the vessel for the casting of the following sample (about 40 sec.). The cycle of progression of the crucibles in the furnace is adapted to this time requirement.

It is well understood that the present invention is not limited to the particular embodiment described. Notably, the elements constituting the apparatus may be replaced by numerous equivalents or modifications of the embodiment without in any way being outside the scope of the present invention. For instance, the tubular shape of the heating enclosure may have a conicity extending in a transverse direction so as to obtain a more intense heating of the crucibles as they progress towards the outlet of the furnace.

Similarly, the geometric forms of the support beams 12 and 13 and of the bars 17 and 18 serving as slideways have been selected only because of the technological simplicity of their manufacture. Elements of different structures could obviously have been utilized to serve the same functions. Also, one could have substituted an integral element of the angle iron type whose horizontal arm would have served as support for the crucibles and whose vertical arm would have fulfilled the function of slideway during the longitudinal displacements and of balustrade during the laternating rotational rockings.

We claim:

1. Apparatus for the automatic preparation of samples for analysis comprising a fusion furnace, a casting device and means for the automatic control of the unfolding of the manufacturing sequence, characterized in that the fusion furnace is constituted by a heating enclosure of tubular form, horizontally disposed and opened, at its two ends to permit, respectively, the introduction and the removal of crucibles with samples in regular alignment and in that the said apparatus is equipped with means of "step by step" transport assuring a periodical progression of the crucibles in the interior of the heating enclosure in successive and repeating stages, and means for agitating the samples during momentary stops of the crucibles in their periodic progression.

2. Apparatus according to claim 1 characterized in that the step-by step transport means are constituted by two distinct parts, respectively mobile and fixed, in the longitudinal direction of the enclosure, and respectively assuring the transfer of the crucibles during their periodic progression and their support during the momentary stops in their progression.

3. Apparatus according to claim 2 characterized in that the said fixed part is constituted by parallel beams extending at least over the entire length of the heating enclosure and separated from each other by a distance less than the width of the crucibles, in that the said longitudinally movable part is constituted by at least one small beam parallel to the previously mentioned fixed beams, disposed between them and also having the possibility of moving vertically so as to be able to be raised or lowered with respect to the said fixed beams, and in that the said beams respectively constituting the fixed part and the part movable in the longitudinal direction of the enclosure have at their upper part a support surface for the support of the crucibles.

4. Apparatus according to claim 2 characterized in that the said part movable in the longitudinal direction of the enclosure is constituted by a single beam extending at least over the entire length of the enclosure.

5. Apparatus according to claim 1 characterized in that it also comprises means for guiding the crucibles during their periodic progression in the heating enclosure in successive and repeating stages.

6. Apparatus according to claim 5 characterized in that the guiding means are constituted by two horizontal slideways extending at least over the entire length of the enclosure and disposed at respective sides of the aligned crucibles and above each of the two beams constituting the said fixed part longitudinally.

7. Apparatus according to claim 1, characterized in that the agitating means are constituted by mechanical elements which are movable transversely to the enclosure and provide pivoting of the crucibles alternatingly from side to side in their direction of transport by an oscillating movement about the said direction.

8. Apparatus according to claim 7 characterized in that the said mechanical agitating elements are constituted by a cradle composed by the fixed part longitudinally and the guiding means extend substantially outside both ends of the enclosure and assembled at their respective ends by arches which are rotatably movable about an axis longitudinal to the heating enclosure.

* * * * *